United States Patent

Kohayakawa et al.

[11] Patent Number: 5,557,321
[45] Date of Patent: Sep. 17, 1996

[54] FUNDUS CAMERA OR OPTHALMIC APPARATUS COMPRISING A FLASH LIGHT SOURCE SYSTEM

[75] Inventors: Yoshimi Kohayakawa, Yokohama; Takeshi Kitamura, Kawasaki, both of Japan

[73] Assignee: Canon Kabushiki Kaisha, Tokyo, Japan

[21] Appl. No.: 435,533

[22] Filed: May 5, 1995

Related U.S. Application Data

[63] Continuation of Ser. No. 85,451, Jun. 10, 1993, abandoned, which is a continuation of Ser. No. 762,934, Sep. 19, 1991, abandoned.

[30] Foreign Application Priority Data

Oct. 2, 1990 [JP] Japan ..................................... 2-264264
Dec. 29, 1990 [JP] Japan ..................................... 2-418432

[51] Int. Cl.$^6$ .................................................... H04N 7/18
[52] U.S. Cl. .................. 348/78; 354/62; 351/206; 351/221
[58] Field of Search ..................................... 351/205, 206, 351/216, 221; 354/62; 348/77, 78; H04N 7/18

[56] References Cited

U.S. PATENT DOCUMENTS

| | | | |
|---|---|---|---|
| 4,149,787 | 4/1979 | Kobayashi et al. | 354/62 |
| 4,184,752 | 1/1980 | Richards et al. | 351/16 |
| 4,257,687 | 3/1981 | Kohayakawa | 351/7 |
| 4,266,861 | 5/1981 | Sawa | 351/7 |
| 4,412,728 | 11/1983 | Sakane | 351/206 |
| 4,429,970 | 2/1984 | Fujiwara | 354/413 |
| 4,526,450 | 7/1985 | Suzuki et al. | 351/206 |
| 4,561,429 | 12/1985 | Sato | 128/6 |
| 4,690,525 | 9/1987 | Kabayashi et al. | 351/206 |
| 4,717,952 | 1/1988 | Kohayakawa et al. | 358/113 |
| 4,762,410 | 8/1988 | Sekiguchi et al. | 351/206 |
| 4,834,526 | 5/1989 | Nunokawa | 351/206 |
| 4,872,029 | 10/1989 | Kato | 354/413 |
| 4,878,750 | 11/1989 | Sekiguchi | 351/212 |
| 5,134,469 | 7/1992 | Uchimura | 348/68 |

FOREIGN PATENT DOCUMENTS 57-183830 11/1982 Japan .................... A61B 3/14

*Primary Examiner*—Yon J. Couso
*Assistant Examiner*—Ngoc-Yen Vu
*Attorney, Agent, or Firm*—Fitzpatrick, Cella, Harper & Scinto

[57] ABSTRACT

A fundus camera includes a first photographing optical system for guiding an image of an eye to be inspected to a first imager, a second photographing optical system for guiding the image of the eye to be inspected to a second imager having a sensitivity different from the sensitivity of the first imager, and a flash light source for photographing adapted to emit an amount of light corresponding to the sensitivity of the first imager and an amount of light corresponding to the sensitivity of the second imager. One of the first and second imagers is an electronic camera.

11 Claims, 8 Drawing Sheets

| | | |
|---|---|---|
| BUTTON A' | OFF/ON | |
| BUTTON B' | OFF/ON | |
| BUTTON C' | OFF/ON | |
| BUTTON D' | OFF/ON | ⊓ |
| QUICK-RETURN MIRROR 28 | IN/OUT | ←TA→ |
| QUICK-RETURN MIRROR 30 | IN/OUT | |
| T1 | OFF/ON | ⊔ |
| T2 | OFF/ON | |
| T3 | OFF/ON | ⊔ |

FUNDUS CAMERA OR OPTHALMIC APPARATUS COMPRISING A FLASH LIGHT SOURCE SYSTEM

BACKGROUND OF THE INVENTION

This application is a continuation of application Ser. No. 08/085,451, filed Jun. 10, 1993, which was a continuation of application Ser. No. 07/762,934, filed Sep. 19, 1991, both now abandoned.

1. Field of the Invention

This invention relates to a fundus camera used, for example, in an ophthalmic hospital or the like.

2. Description of the Prior Art

In a conventional fundus camera, an image of a fundus (an eyeground) is recorded on a film having a certain resolution. Such a camera, however, cannot be used for an immediate diagnosis, since it is necessary to develop the film. Hence, there has been proposed a system which performs video photographing using a television camera while illuminating a fundus with a light source for observation, or a system which performs video photographing while illuminating a fundus with a flash lamp for film photographing, as disclosed in Japanese Patent Application Public Disclosure (Kokai) No. 57-183830 (1982).

However, in the above-described system which performs video photographing using the light source for observation, an image having a sufficient resolution cannot be obtained due to an insufficient amount of light. In the system which performs video photographing using the flash lamp for film photographing, a half-mirror is fixedly disposed in the optical path. Hence, the method of the use, and the range of application of the system are limited. That is, since a light beam produced by single emission is divided by the half-mirror, the amount of light for a fundus image is insufficient. Furthermore, the distribution ratio of the light beam is previously set in accordance with the amount of light suitable for the sensitivity of each of an electronic camera and a film camera to be used. Hence, if the electronic camera or the film camera to be used is replaced with another camera, it is impossible to deal with the sensitivity of the other camera.

SUMMARY OF THE INVENTION

It is an object of the present invention to solve the above-described problems.

It is another object of the present invention to provide a fundus camera which can peform video photographing or film photographing having a high resolution, and which has a wide range of applications.

It is still another object of the present invention to provide a fundus camera which can record images of a fundus continuously or selectively in both of an electronic camera and a film camera.

According to one aspect, the present invention which achieves these objectives, relates to a fundus camera, comprising a first photographing optical system for guiding an image of an eye to be inspected to first image means, a second photographing optical system for guiding the image of the eye to be inspected to sescond imaging means having a sensitivity different from the sensitivity of the first imaging means, and a flash light source for photographing adapted to emit an amount of light corresponding to the sensitivity of the first imaging means and an amount of light corresponding to the sensitivity of the second imaging means. One of the first and second imaging means comprises an electronic camera.

According to still another aspect, the present invention which achieves these objectives, relates to a fundus camera, comprising a first photographing optical system for guiding an image of an eye to be inspected to first imaging means, a second photographing optical system for guiding the image of the eye to be inspected to second imaging means having a sensitivity different from the sensitivity of the first imaging means, and a flash light source for photographing adapted to perform two successive emissions of light, the amount of light emitted during one of the two successive emissions corresponding to the sensitivity of the first imaging means and the amount of light emitted during the other of the two successive emissions corresponding to the sensitivity of the second imaging means. One of the first and second imaging means comprises an electronic camera.

According to still another aspect, the present invention which achieves these objectives relates to a fundus camera, comprising a first photographing optical system for guiding an image of an eye to be inspected to first imaging means, a second photographing optical system for guiding the image of the eye to be inspected to second imaging means having a sensitivity different from the sensitivity of the first imaging means, and a flash light source for photographing adapted to perform two successive emissions of light, the amount of light emitted during one of the two successive emissions corresponding to the sensitivity of the first imaging means and the amount of light emitted during the other of the two successive emissions corresponding to the sensitivity of the second imaging means. One of the first and second imaging means comprises means for immediately displaying the image of the eye.

According to still another aspect, the present invention which achieves these objectives relates to an ophthalmic apparatus, comprising a first photographing optical system for guiding an image of an eye to be inspected to first imaging means, a second photographing optical system for guiding the image of the eye to be inspected to second imaging means having a sensitivity different from the sensitivity of the first imaging means, and a flash light source for photographing adapted to emit an amount of light corresponding to the sensitivity of the first imaging means and an amount of light corresponding to the sensitivity of the second imaging means. One of the first and second imaging means comprises an electronic camera.

According to still another aspect, the present invention which achieves these objectives relates to an ophthalmic apparatus, comprising a first photographing optical system for guiding an image of an eye to be inspected to first imaging means, a second photographing optical system for guiding the image of the eye to be inspected to second imaging means having a sensitivity different from the sensitivity of the first imaging means, and a flash light source for photographing adapted to perform two successive emissions of light, the amount of light emitted during one of the two successive emissions corresponding to the sensitivity of the first imaging means and the amount of light emitted during the other of the two successive emissions corresponding to the sensitivity of the second imaging means. One of the first and second imaging means comprises an electronic camera.

According to still another aspect, the present invention which achieves these objectives relates to an ophthalmic apparatus, comprising a first photographing optical system for guiding an image of an eye to be inspected to first imaging means, a second photographing optical system for guiding the image of the eye to be inspected to second imaging means having a sensitivity different from the sensitivity of the first imaging means, and a flash light source for photographing adapted to perform two successive emissions of light, the amount of light emitted during one of the two successive emissions corresponding to the sensitivity of the first imaging means and the amount of light emitted during the other of the two successive emission corresponding to the sensitivity of the second imaging means. One of the first and second imaging means comprises means for immediately displaying the image of the eye.

DETAILED DESCRIPTION OF THE PREFERRED EMBODIMENTS

The present invention will now be explained in detail with reference to the preferred embodiments illustrated in the drawings.

Figure 1:
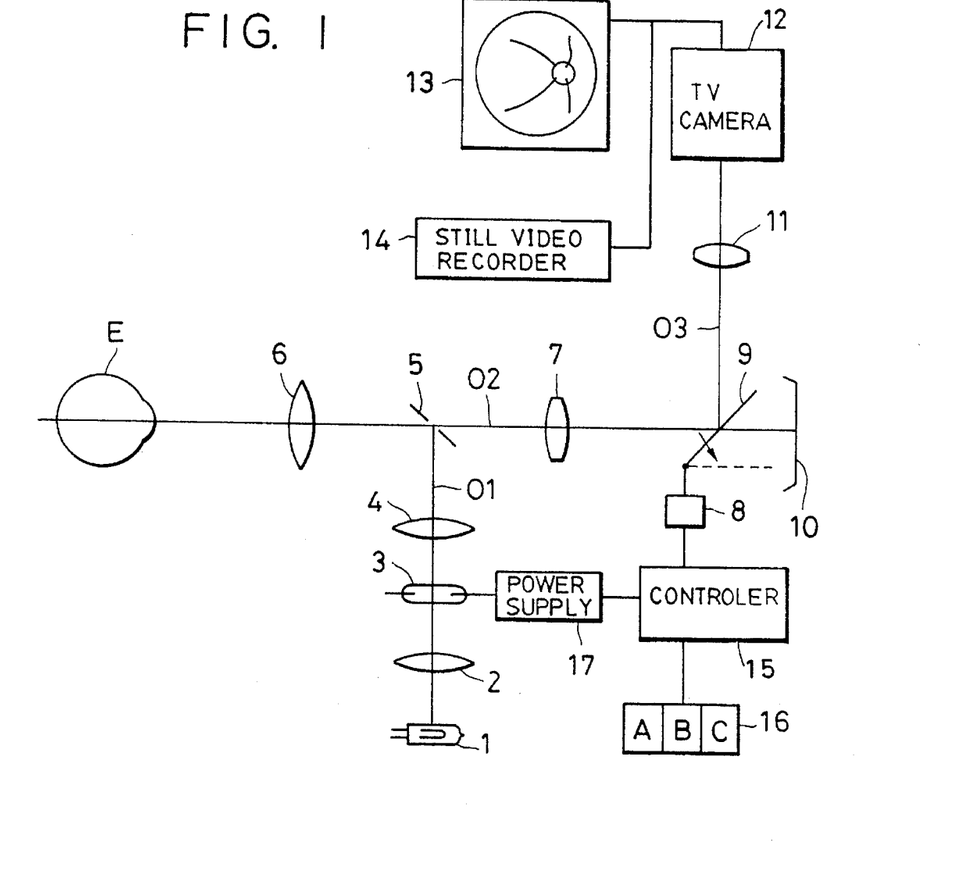
FIG. 1 illustrates a schematic view of the configuration of a first embodiment of the present invention.

FIG. 1 illustrates the configuration of a first embodiment of the present invention. In FIG. 1, a condenser lens 2, a stroboscopic light source 3 for photographing, conjugate to the pupil of an eye E to be inspected, a lens 4, a perforated mirror 5, and a lens 6 are sequentially arranged on an optical path 01 from a light source 1 for observing a fundus, such as an incandescent lamp or the like, to the eye E. A lens 7, an insertable quick-return mirror 9 connected to a solenoid 8, and a film 10 provided within a camera are arranged on an optical path 02 behind the perforated mirror 5. A lens 11 and a television camera 12 are arranged on an optical path 03 in the direction of reflection of the quick-return mirror 9. The output of the television camera 12 is connected to a television monitor 13 and a still-video recording means 14. The output of a controller 15 is connected to the solenoid 8. The controller 15 is connected to a power supply 17 and photographing-mode buttons 16 which, when pressed, cause the apparatus to operate in modes A, B and C, respectively. The output of the power supply 17 is connected to the stroboscopic light source 3 for photographing.

When observing a fundus, the light source 1 for observing the fundus is lit and the quick-return mirror 9 is disposed on the optical path 02, and the light beam from the light source 1 advances on the optical path 01. The light beam passes through the condenser lens 2 and the lens 4, is reflected by the perforated mirror 5, and reaches the eye E to be inspected via the lens 6. The light beam reflected by the fundus returns on the same optical path, passes through the perforated mirror 5 and the lens 7, is reflected by the quick-return mirror 9, and is imaged on the television camera 12 by the lens 11. A fundus image is displayed on the television monitor 13.

Three modes may be selected in photographing the fundus. If the button A among the photographing-mode buttons 16 is depressed, the controller 15 drives the solenoid 8 to retract the quick-return mirror 9 from the optical path 02, and turns on the power supply 17 to light the stroboscopic light source 3 for photographing. The flash light beam emitted from the stroboscopic light source 3 for photographing advances on the same optical path as the light from light source 1 when observing the fundus. The entire light beam reflected by the fundus is projeced onto the film 10 to perform film photographing. If the button B is depressed, video photographing is performed with the quick-return mirror 9 inserted in the optical path 02. An image of the fundus is recorded on the still-video recording means 14, and at the same time is displayed on the television monitor 13. If the button C is depressed, video photographing is first performed, and film photographing is performed immediately after the completion of the video photographing. The time interval between these two photographing operations equals the time needed for moving the solenoid 8, and is therefore very short. In practice, in order to prevent the movement of the eye E, the opening and closing of the pupil, and miosis during this time interval, it is preferred that two capacitors are provided within the power supply 17, and the stroboscopic light source 3 for photographing is continuously lit by sequentially discharging the capacitors.

Figure 2:
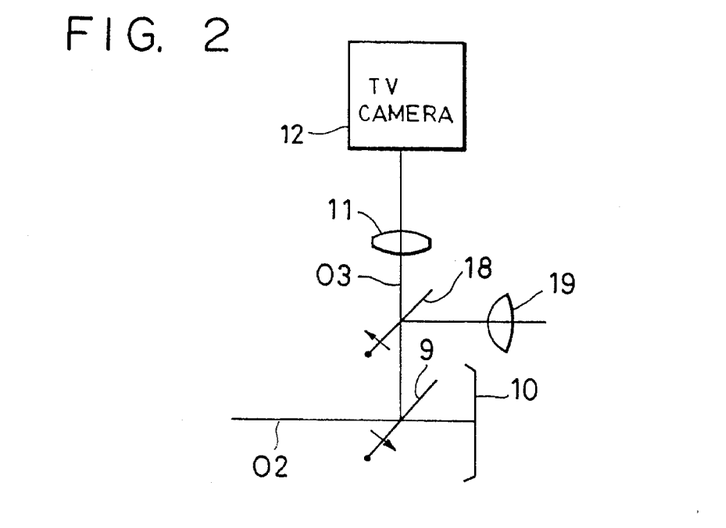
FIG. 2 illustrates a schematic view of the configuration of the principal part of a second embodiment of the present invention.

FIG. 2 illustrates the configuration of the principal part of another embodiment. In FIG. 2, a second quick-return mirror 18 insertable in the optical path 03 by a driving means (not shown) is disposed between the quick-return mirror 9 and the lens 11 on the optical path 03, and an eyepiece 19 is disposed in the direction of reflection of the quick-return mirror 18 to provide an optical finder unit. Other components are the same as those in the first embodiment.

In this embodiment, it is possible to observe the fundus via the eye-piece 19 by inserting the second quick-return mirror 18. In fluorescence photographing, since the lightness of a fundus image is low, it is desirable to perform both video and film photographing operations in the mode actuated by depressing the button C while observing the image through the eye-piece 19.

It is necessary to use well-known filters in fluorescence photographing and non-mydriasis photographing, but an explanation thereof will be omitted.

In still another embodiment, a fourth button is provided in addition to the buttons A, B and C. When the fourth button is depressed and selected, the quick-return mirror 9 shown in FIG. 1 retracts, and an image is photographed on the film at the first depressing operation of a shutter button. At the second depressing operation of the shutter button, the quick-return mirror 9 remains in the position shown by a solid line in FIG. 1, and video recording is performed. After the third depressing operation of the shutter button, film/video photographing is automatically switched (the time interval may be arbitrarily selected). As a result, film photographing is performed immediately after the completion of video photographing. In this embodiment, the stroboscopic light source 3 performs a single emission operation at every shutter releasing operation, and emits an amount of light corresponding to each sensitivity.

Figure 3:
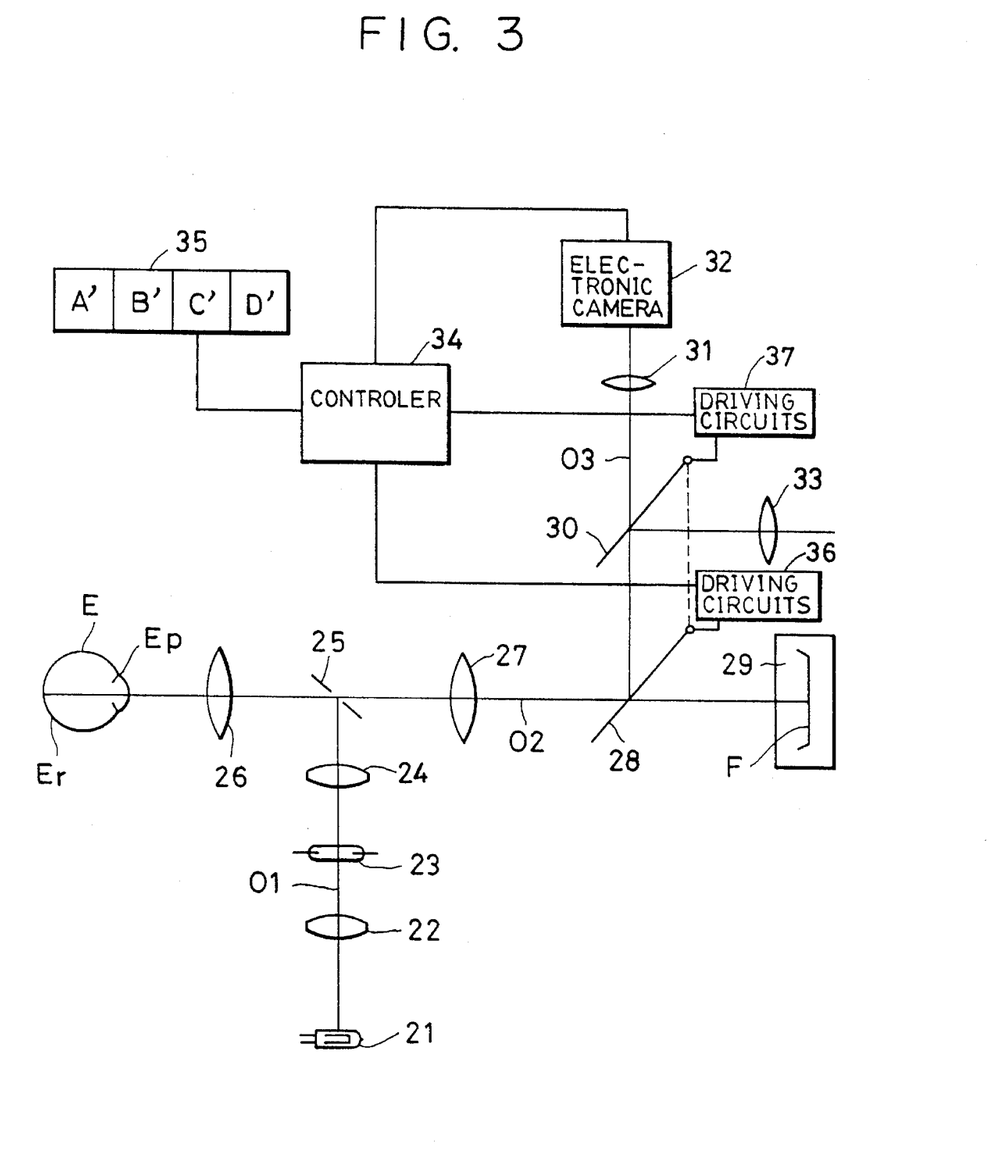
FIG. 3 is a schematic view illustrating the configuration of a third embodiment of the present invention.

FIG. 3 illustrates the configuration of a third embodiment of the present invention. A lens 22, a flash light source 23 for photographing, comprising a xenon tube, whose amount of light is variable, as will be described later, a lens 24, a perforated mirror 25 and an objective lens 26 are arranged on an optical path 01 from a continuously-lit light source 21 for observation of an eye E to be inspected. A lens 27, a quick-return mirror 28 and a film F in a film camera 29 are arranged on an optical path 02 behind the perforated mirror 25. An optical finder 33 is disposed in the direction of reflection of a quick-return mirror 30. A control means 34 is provided for the control of the entire fundus camera. An electronic camera 32, a photographing-mode selection means 35 having four buttons, and driving circuits 36 and 37 are connected to the control means 34. The outputs of the driving circuits 36 and 37 are connected to the quick-return mirrors 28 and 30, respectively. The quick-return mirrors 28 and 30 are insertable in the optical paths 02 and 03 by the driving circuits 36 and 37, respectively. The light source 21 for observation is conjugate with the flash light source 23 for photographing with respect to the lens 22. The flash light source 23 for photographing is conjugate to the perforated mirror 25 with respect to the lens 24, and is also conjugate with the pupil Ep of the eye E to be inspected with respect to the objective lens 26.

Figure 4:
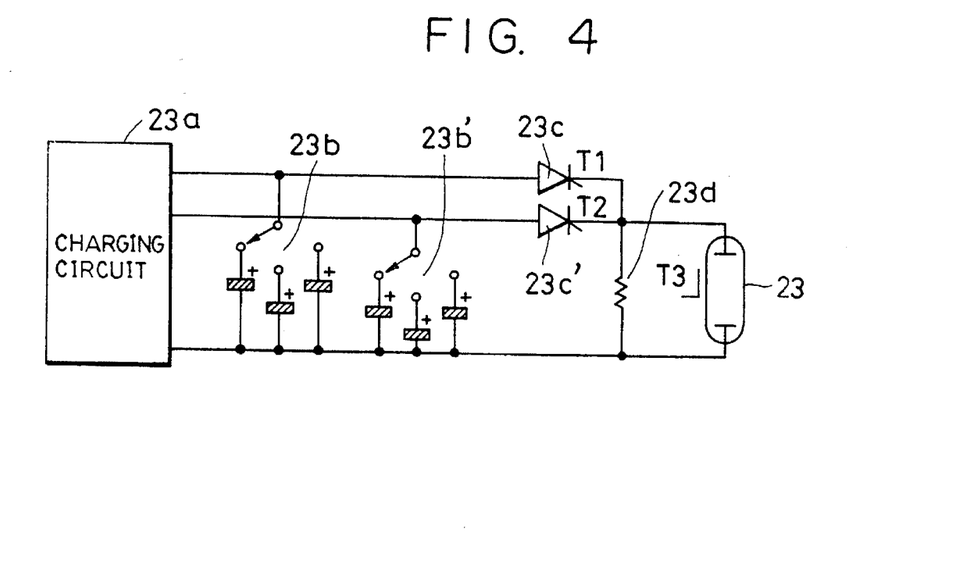
FIG. 4 is a schematic view illustrating the configuration of a light-amount adjusting circuit for a flash light source for photographing.

FIG. 4 illustrates the configuration of a light-amount adjusting circuit for the flash light source 23 for photographing. In FIG. 4, stroboscopic capacitors 23b and 23b' for photographing, thyristors 23c and 23c', a resistor 23d, and the flash light source 23 for photographing are connected to a charging circuit 23a. Electric charges charged in the stroboscopic capacitors 23b or 23b' are transmitted to the flash light source 23 for photographing through the thyristors 23c and 23c'. Although not illustrated in FIG. 4, the control means 34 is connected to the above-described components. Each of the stroboscopic capacitors 23b and 23b' comprises a plurality of capacitors. The control means 34 may arbitrarily select capacitors, whereby the capacities of the capacitors 23b and 23b' may be varied. The control means 34 inputs trigger signals to the thyristors 23c and 23c'.

In an observation/positioning operation, the driving circuits 36 and 37 insert the quick-return mirrors 28 and 30 in the optical paths 02 and 03, respectively, and lights the light source 21 for observation. The light beam from the light source 21 for observation advances on the optical path 01, passes through the lens 22, the flash light source 23 for photographing, and the lens 24, is reflected by the perforated mirror 25, and is incident upon the eye E to be inspected via the objective lens 26. The light beam reflected by the fundus returns on the same optical path, passes through an opening of the performated mirror 25 and the lens 27, is reflected by the quick-return mirrors 28 and 30, and reaches the optical finder 33. The inspector performs positioning while observing a fundus image.

In the present embodiment, it is possible to perform three kinds of photographing in three different photographing modes, that is, photographing only with the film camera 29, photographing only with the electronic camera 32, and photographing by both the film camera 29 and the electronic camera 32. These photographing modes are selected by depressing, respectively, push buttons A', B' and C' of the photographing-mode selection means 35. A push button D' serves as a photographing button.

Figure 5:
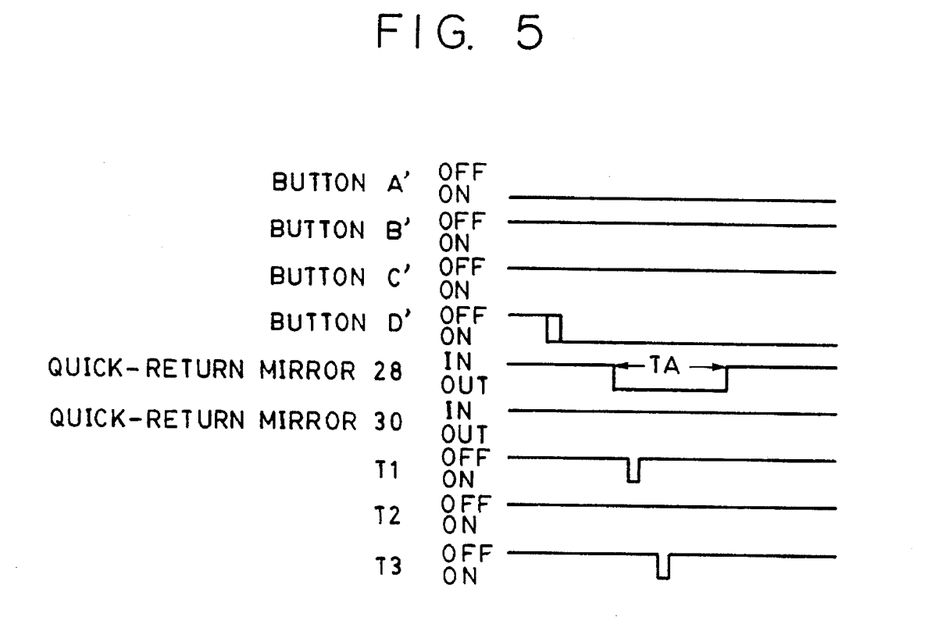
FIG. 5 a schematic view illustrating the operational states of different elements in different photographing modes of a film camera in the third embodiment.
Figure 6:
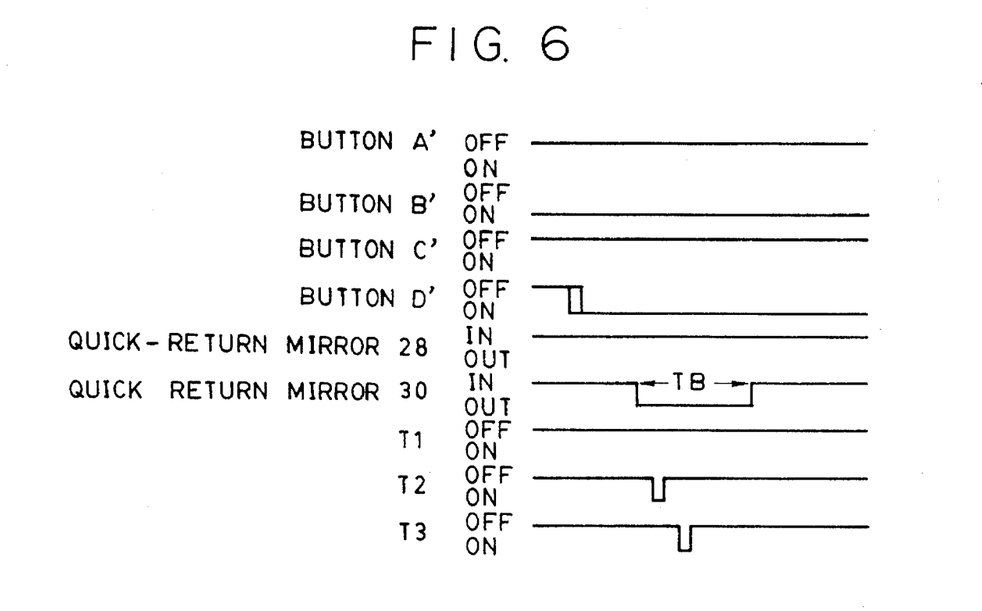
FIG. 6 is a schematic view illustrating the operationsal states of elements in different photographing modes of an electronic camera in the third embodiment.
Figure 7:
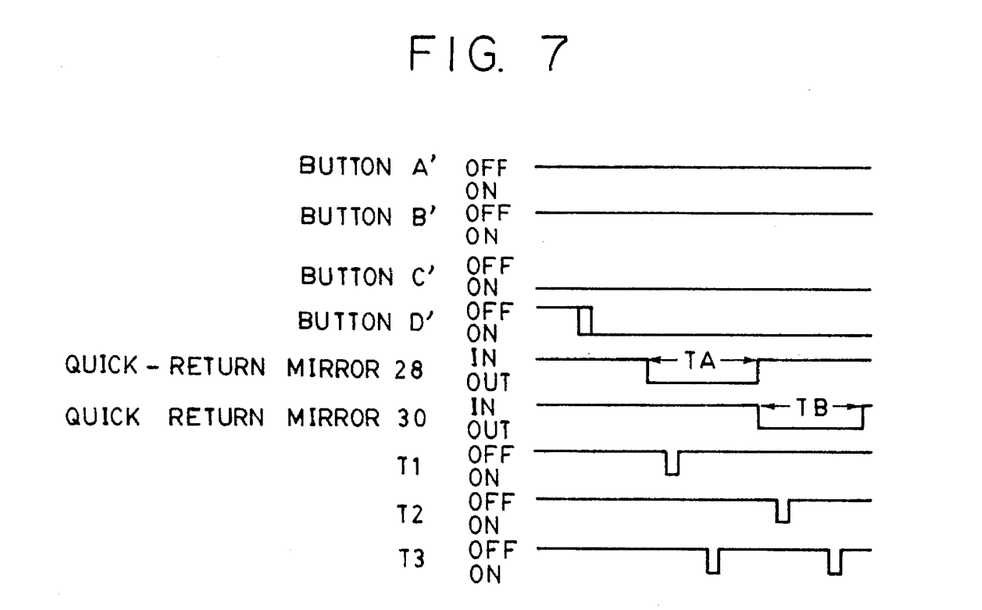
FIG. 7 is a schematic view illustrating the operationsal states of elements in different photographing modes of the film camera and the electronic camera in the third embodiment.

FIGS. 5–7 illustrate operational states of respective members in respective photographing modes with the abscissa representing time. In FIGS. 5–7 (and also in FIGS. 9–11 and 13–15), symbols T1, T2 and T3 represent on-off states of trigger signals to be input from the control means 34 to the thyristors 23c and 23c', and the flash light source 23 for photographing, respectively. It is assumed that before photographing, the capacities of the stroboscopic capacitors 23b and 23b' for photographing have been changed in accordance with the sensitivities of the film F and the electronic camera 32, respectively, and electric charges necessary for photographing have been charged in the stroboscopic capacitors 23b and 23b' for photographing.

When performing photographing only with the film camera 29, the push button A' of the photographing-mode selection means 35 is switched on, and the photographing button D' is switched on after the completion of positioning, as shown in FIG. 5. The quick-return mirror 28 is retracted from the optical path 02 during a time period TA, during which the control means 34 sequentially inputs pulse signals T1 and T3 to the thyristor 23c and the flash light source 23 for photographing, and electric charges charged in the stroboscopic capacitor 23b for photographing are instantaneously discharged to light the flash light source 23 for photographing. The light beam from the flash light source 23 advances in the same manner as during observation, and a fundus image is recorded by the film camera 29.

When performing photographing only with the electronic camera 32, the push button B' of the photographing-mode selection means 35 is switched on, and the photographing button D' is switched on after the completion of positioning, as shown in FIG. 6. The quick-return mirror 30 is retracted from the optical path 03 during a time period TB, during which pulse signals T2 and T3 are sequentially input to the thyristor 23c' and the flash light source 23 for photographing, the flash light source 23 for photographing is lit by electric charges charged in the stroboscopic capacitor 23b' for photographing, and a fundus image is recorded by the electronic camera 32.

When performing photographing with both the film camera 29 and the electronic camera 32, the push button C' of the photographic-mode selection means 35 is switched on, and the photographing button D' is then switched on, as shown in FIG. 7, whereby the above-described successive recording with the film camera 29 and the electronic camera 32 is performed.

Specifically, when the push button C' is switched on and the photographing button D' is switched on the quick return mirror 28 is retracted out of the optical path 02 during a time period TA during which the control means 34 sequentially inputs pulse signals T1 and T3 to the thyristor 23*c* and the flash light source 23 for photographing, and electric charges charged in the stroboscopic capacitor 23*b* for photographing are instantaneously discharged to light the flash light source 23 for photographing. The light beam from the flash light source then advances along the optical. path 02 and a fundus image is recorded by the film camera 29. Immediately thereafter, quick-return mirror 28 is moved into the optical path 02 and quick-return mirror 30 is retracted out of the optical path 03 during a time period TB, during which pulse signals T2 and T3 are sequentially input to the thyristor 23*c*' and the flash light source 23 for photographing, the flash light source 23 for photographing is lit by electric charges charged in the stroboscopic capacitor 23*b*' for photographing, and a fundus image is recorded by the electric camera 32.

As described above, in the present embodiment, the stroboscopic capacitors 23*b* and 23*b*' are separately provided for recording with the film camera 29 and the electronic camera 32, and the capacities of the capacitors 23*b* and 23*b*' may be varied by the control means 34. Hence, by changing the capacities of the capacitors 23*b* and 23*b*' in accordance with the sensitivities of the film F and the electronic camera 32, the amount of light emitted by the flash light source 23 for photographing may be changed. As a result, it is possible to obtain a clear fundus image not having an excessive or insufficient amount of light, and to arbitrarily change the distribution ratio of the amount of light for each photographing operation.

Alternatively, the capacities of the stroboscopic capacitors 23*b* and 23*b*' for photographing may be constant, and the amount of light from the flash light source 23 for photographing may be changed by interrupting the emission current.

Figure 8:
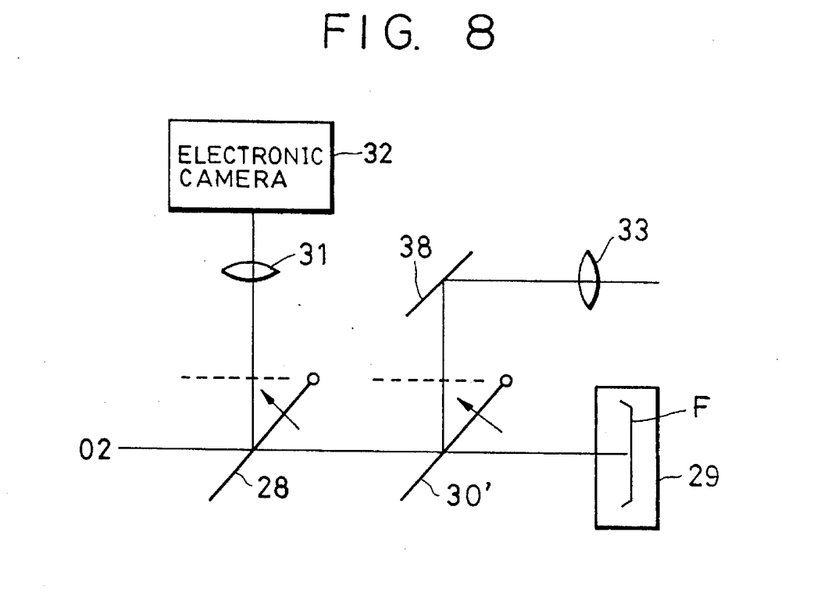
FIG. 8 a schematic view illustrating the configuration of the principal part of a fourth embodiment of the present invention.

The positions of insertion of the quick-return mirrors 28 and 30 are not limited to the positions shown in the third embodiment. As shown in FIG. 8 illustrating the configuration of the principal part of a fourth embodiment, a quick-return mirror 30' may be disposed on the optical path 02 behind the quick-return mirror 28, a mirror 38 may be disposed in the direction of reflection of the quick-return mirror 30', and an optical finder 33 may be disposed in the direction of reflection of the mirror 38.

Figure 9:
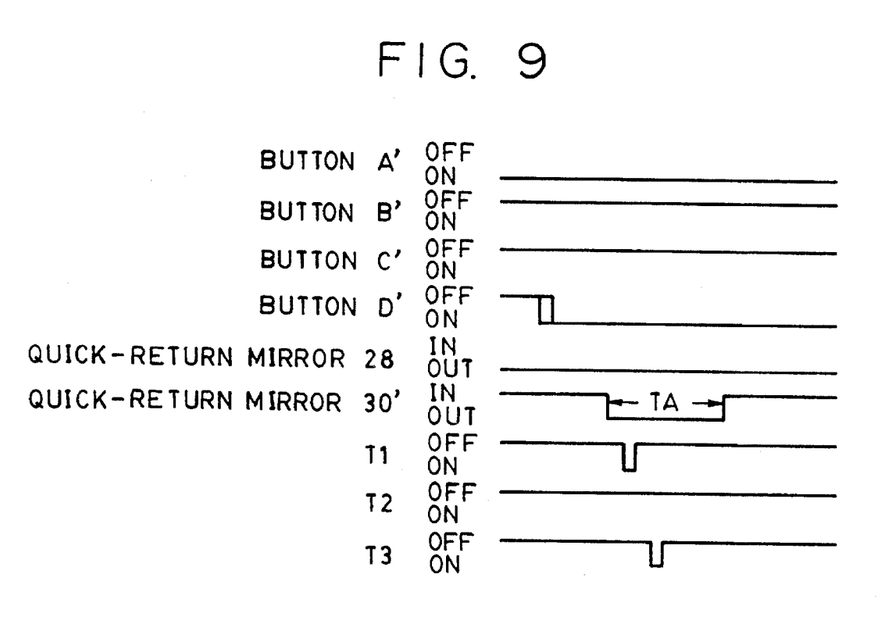
FIG. 9 is a schematic view illustrating the operational states of elements in different photographing modes of a film camera in the fourth embodiment.
Figure 10:
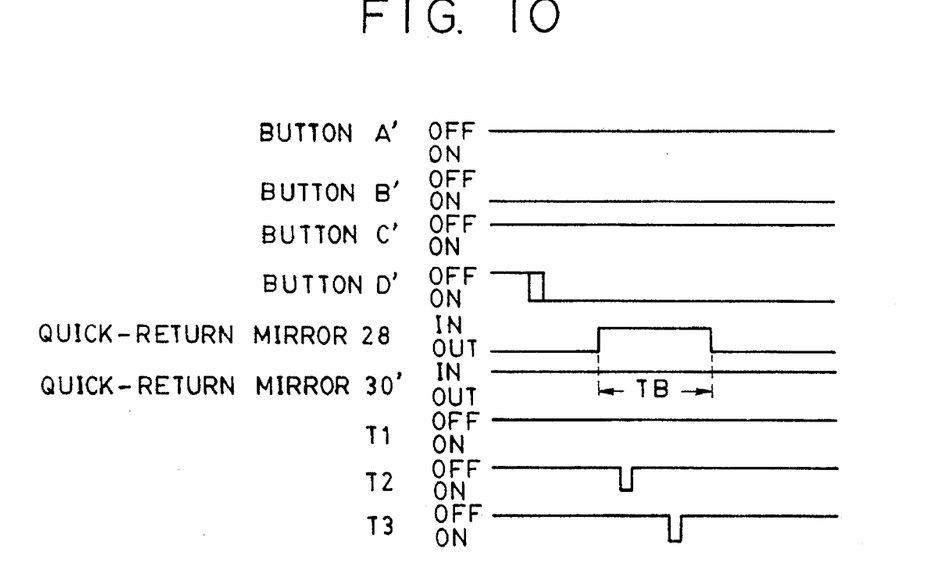
FIG. 10 is a schematic view illustrating the operational states of elements in different photographing modes of an electronic camera in the fourth embodiment.
Figure 11:
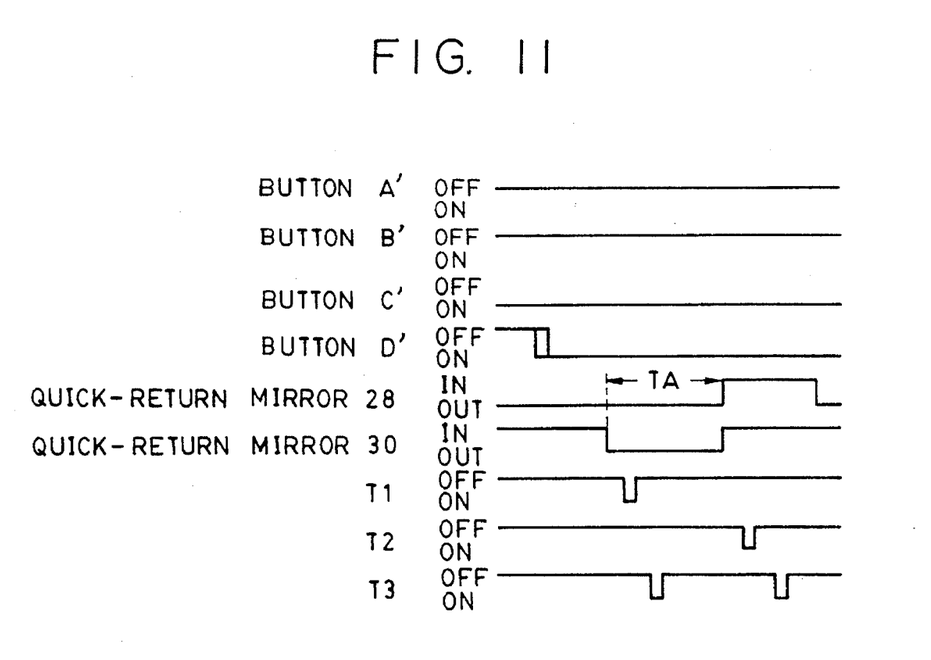
FIG. 11 is a schematic view illustrating the operational states of elements in different photographing modes of the film camera and the electronic camera in the fourth embodiment.

The operations of the respective members in the respective photographing modes in the fourth embodiment are shown in FIGS. 9–11. When performing photographing only with the film camera 29, the push button A' of the photographing-mode selection means 35 is switched on and the photographing button D' is switched on after the completion of the positioning, as shown in FIG. 9. The quick-return mirror 28 is retracted out of the optional path 02 during this entire operation, while the quick-return mirror 30' is retracted from the optical path 02 during a time period TA during which the control means 34 sequentially inputs pulse signals T1 and T3 to thyristor 23*c* and a flash light source 23 for photographing, and electric charges charged in the stroboscopic capacitor 23*b* for photographing are instantaneously discharged to light the flash light source 23 for photographing. The light beams from flash light source 23 advance in the same manner as during an observation operation, and fundus image is recorded by the film camera 29.

When performing photographing with only the electronic camera 32, the push button B' of the photographing-mode selection means 35 is switched on and the photographing button D' is switched on after the completion of positioning, as shown in FIG. 10. The quick-return mirror 28 is moved from a retracted position out of the optical path 02 to a position in the optical path during a time period TB, during which pulse signals T2 and T3 are sequentially input to the thyristor 23*c*' and the flash light source 23 for photographing, the flash light source 23 for photographing is lit by the electric charges charged in the stroboscopic capacitor 23*b*' for photographing, and the fundus image is recorded by the electronic camera 32.

When performing photographing with both the film camera 29 and the electronic camera 32, the push button C' of the photographic-mode selection means 35 is switched on and the photographing button D' is switched on after the completion of positioning, as shown in FIG. 11. The quick-return mirror 30 is retracted out of the optical path 02 during the time period TA. During this time period the quick-return mirror 22 is also maintained in a position retracted out of the optical path 02 thereby permitting photographing with the film camera 29. At the beginning of time period TA pulse signal T1 is input to the thyristor 23*c* and pulse signal T3 is input to the flash light source 23 for photographing, whereby the flash light source 23 for photographing is lit by the electric charges charged in the stroboscopic capacitor 23*b* for photographing, and a fundus image is recorded by the film camera 29. Immediately thereafter, the quick-return mirror 30 and the quick-return mirror 28 are moved into the optical path 02, during which pulse signals T2 and T3 are sequentially input to the thyristor 23*c*' and the flash light source 23 for photographing, the flash light source 23 for photographing is lit by the electric charges charged in the stroboscopic capacitor 23*b*' for photographing and a fundus image is recorded by the electronic camera 32.

Although the operations of insertion and retraction of the quick-return mirrors 28 and 30' are more or less different from the operations in the third embodiment, the procedure of emission of light from the flash light source 23 for photographing is the same as in the third embodiment.

Figure 12:
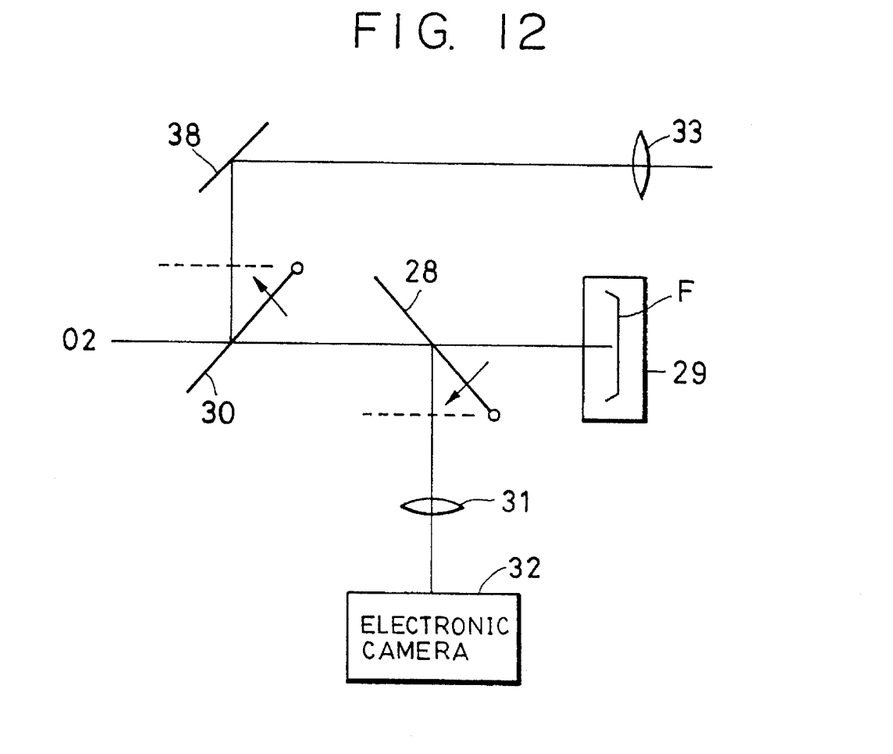
FIG. 12 is a schematic view illustrating the configuration of the principal part of a fifth embodiment of the present invention.

Alternatively, as shown in FIG. 12 illustrating the configuration of the principal part of a fifth embodiment, a quick-return mirror 30" may be disposed on the optical path 02 in front of the quick-return mirror 28, a mirror 38 may be disposed in the direction of reflection of the quick-return mirror 30", and the optical finder 33 may be disposed in the direction of reflection of the mirror 38.

Figure 13:
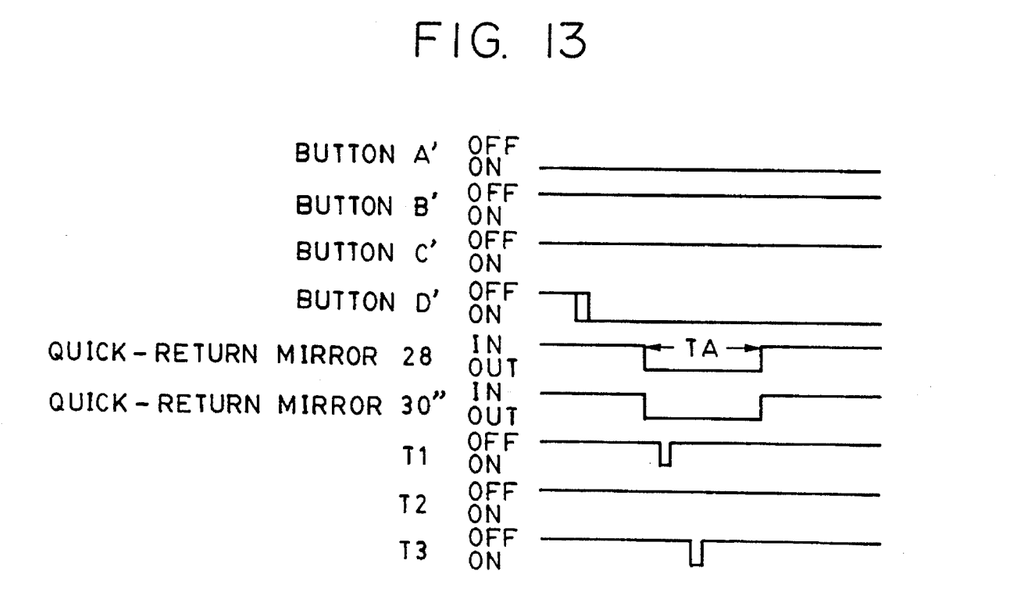
FIG. 13 is a schematic view illustrating the operational states of elements in different photographing modes of a film camera in the fifth embodiment.
Figure 14:
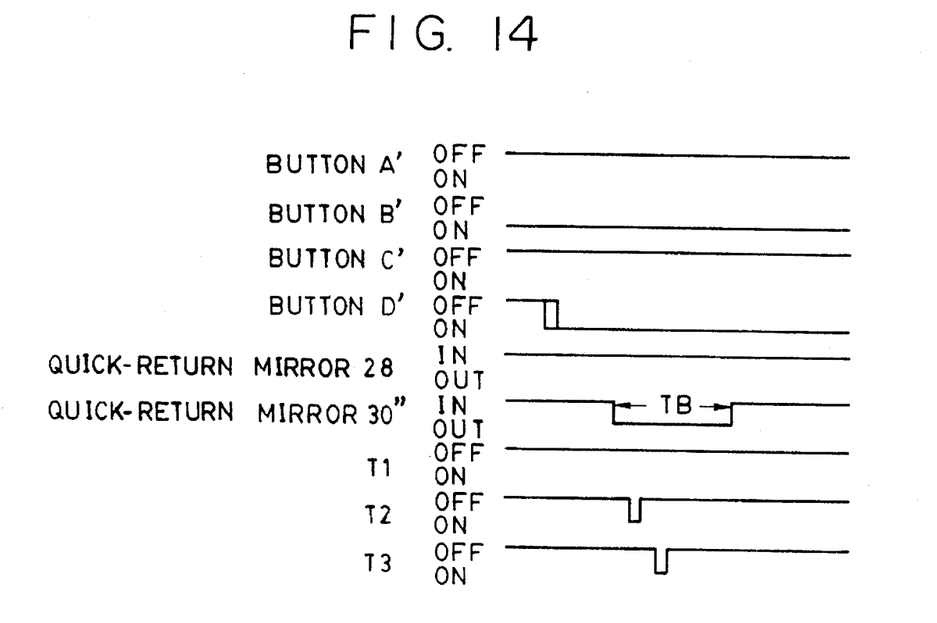
FIG. 14 is a schematic view illustrating the operational states of elements in different photographing modes of an electronic camera in the fifth embodiment.
Figure 15:
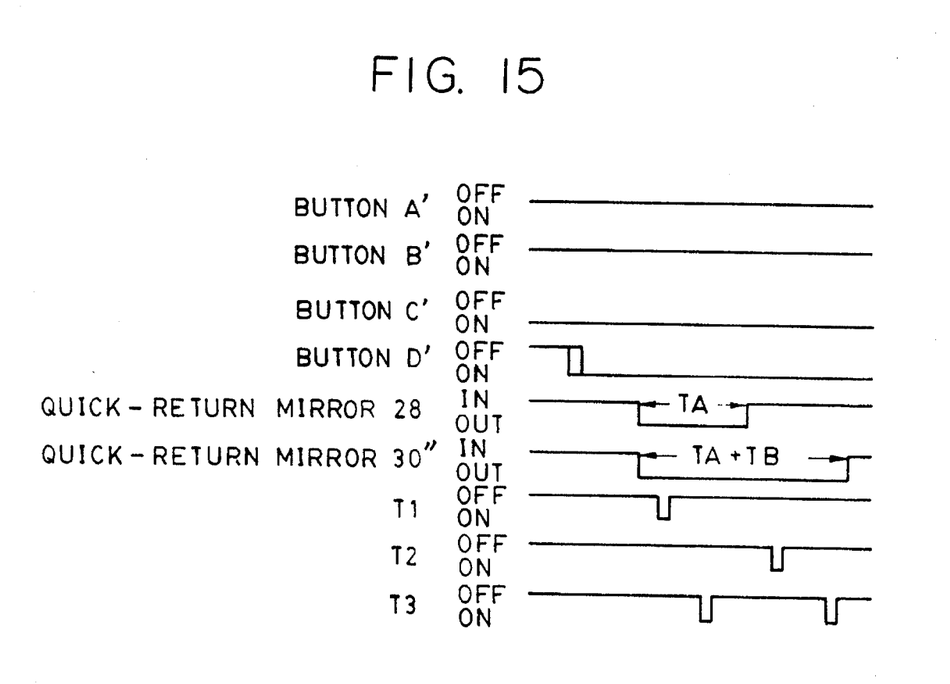
FIG. 15 is a schematic view illustrating the operational states of elements in different photographing modes of the film camera and the electronic camera in the fifth embodiment.

FIGS. 13–15 illustrate the operations of the respective members in the respective photographing modes in the fifth embodiment.

When performing photographing with only the film camera 29 the push button A' of the photographing-mode selection means 35 is switched on and the photographing button D' is switched on after the completion of positioning, as shown in FIG. 13. The quick-return mirror 28 is retracted out of the optical path 02 during the time period TA and the quick-return mirror 30" is also retracted out of the optical path 02 during the time period TA, during which the control means 34 sequentially inputs pulse signals T1 and T3 to the thyristor 23c and the flash light source 23 for photographing, and electric charges charged in the stroboscopic capacitor 23b for photographing are instantaneously discharged to light the flash light source for photographing. The light beam from the flash light source 23 advances along optical path 02 and a fundus image is recorded by the film camera 29.

When performing photographing with only the electronic camera 32 the push button B' of the photographing-mode selection means 35 is switched on and the photographing button D' is switched on after the completion of positioning, as shown in FIG. 14. The quick-return mirror 28 is in the optical path 02 and the quick-return mirror 30" is retracted from the optical path 02 during a time period TB during which the pulse signals T2 and T3 are sequentially input to the thyristor 23c' and the flash light source 23 for photographing, the flash light source 23 for photographing is lit by electric charges charged in the stroboscopic capacitor 23b' for photographing, and a fundus image is recorded by the electronic camera 32.

When performing photographing with both the film camera 29 and the electronic camera 32, the push button C' of the photographic-mode selection means 35 is switched on and the photographing button D' is then switched on, as shown in FIG. 15. The quick-return mirror 28 is retracted from the optical path 02 during a time period TA and a quick-return mirror 30" is retracted from the optical path 02 during a longer time period TA+TB. During the time TA when the quick-return mirror 28 and the quick-return mirror 30" are both retracted out of the optical path 02, pulse signals T1 and T3 are sent by the control means 34, sequentially, to the thyristor 23c and the flash light source 23 for photographing, and electric charges charged in the stroboscopic capacitor 23b for photographing are instantaneously discharged to light the flash light source 23 for photographing. The light beam from the flash light source 23 advances therefore along optical path 02 and the fundus image is recorded by the film camera 29. Immediately thereafter, the quick-return mirror 28 is placed into the optical path 02 while quick-return mirror 30" is maintained out of the optical path 02, during which pulse signals T2 and T3 are sequentially input to the thyristor 23c' and the flash light source 23 for photographing and the flash light source 23 for photographing and the flash light source 23 for photographing is lit by electric charges charged in the stroboscopic capacitor 23b' for photographing and a fundus image is then recorded by the electronic camera 32.

The fundus camera according to each of the above-described embodiments provides a flash light source for photographing which can perform two successive emissions with the amount of light suitable for the sensitivity of an electronic camera and the amount of light suitable for the sensitivity of a film camera. A fundus image illuminated by the flash light source for photographing is guided to the electronic camera photographing optical system or the film camera, photographing optical system by the quick return mirrors. Hence, it is possible to record fundus images in both the electronic camera and the film camera without having a deviation in timing with the amounts of light suitable for the respective sensitivities of the electronic camera and the film camera to be used. As a result, the recorded fundus image does not have an insufficient amount of light.

In the present invention, an instantaneously developing film camera may be used in place of the electronic camera as an immediately visualizing means.

The individual components represented by the blocks shown in FIGS. 1–4, 8 and 12 are well known in the camera art and in the ophthalmological apparatus art and their specific construction and operation is not critical to the invention or the best mode for carrying out the invention. Moreover, the operations discussed in the specification and shown in FIGS. 5–7, 9–11, and 13–15 can be easily programmed into well known controllers or central processing units by persons of ordinary skill in the art and since such programming per se is not part of the invention, no further description thereof is deemed necessary.

What is claimed is:

1. A fundus camera, comprising:
   a first photographing optical system for guiding an image of an eye to be inspected to first imaging means;
   a second photographing optical system for guiding the image of the eye to be inspected to second imaging means having a sensitivity different from the sensitivity of the first imaging means;
   a flash light source system for providing flash illuminations for photographing adapted to emit a quantity of flash light corresponding to the sensitivity of the first imaging means, and a quantity of flash light corresponding to the sensitivity of the second imaging means; and
   select means for selecting one of a plurality of photographing modes, said photographing modes at least comprising a mode for successively alternately performing photographic operations using the first and second imaging means in response to only one manual input operation, wherein each photographic operation is performed with the quantity of flash light of illumination corresponding to the sensitivity of the imaging means used by said flash light source system,
   wherein one of the first and second imaging means comprises an electronic camera.

2. A fundus camera, comprising:
   a first photographing optical system for guiding an image of an eye to be inspected to first imaging means;
   a second photographing optical system for guiding the image of the eye to be inspected to second imaging means having a sensitivity different from the sensitivity of the first imaging means;
   a flash light source system for providing flash illuminations for photographing adapted to perform two successive emissions of light, a quantity of flash light emitted during one of the two successive emissions corresponding to the sensitivity of the first imaging means and the quantity of flash light emitted during the other of the two successive emissions corresponding to the sensitivity of the second imaging means; and
   control means for performing successive alternate photographing operations with the first and second imaging means corresponding to the two successive emissions in response to only one manual input operation,
   wherein one of the first and second imaging means comprises an electronic camera.

3. A fundus camera, comprising:
   a first photographing optical system for guiding an image of an eye to be inspected to first imaging means;
   a second photographing optical system for guiding the image of the eye to be inspected to second imaging means having a sensitivity different from the sensitivity of the first imaging means;
   a flash light source system for providing flash illuminations for photographing adapted to perform two successive emissions of light, a quantity of flash light emitted during one of the two successive emissions corresponding to the sensitivity of the first imaging means and the quantity of flash light emitted during the other of the two successive emissions corresponding to the sensitivity of the second imaging means; and control means for performing successive alternate photographing operations with first and second imaging means corresponding to the two successive emissions in response to only one manual input operation, wherein one of the first and second imaging means comprises means for immediately displaying the image of the eye.

4. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

a flash light source system for providing flash illuminations for photographing adapted to emit a quantity of flash light corresponding to the sensitivity of the first imaging means, and a quantity of flash light corresponding to the sensitivity of the second imaging means; and select means for selecting one of a plurality of photographing modes, said photographing modes at least comprising a mode for successively alternately performing photographing operations by using the first and second imaging means in response to only one manual input operation, wherein each photographic operation is performed with the quantity of flash light of illumination corresponding to the sensitivity of the imaging means used by said flash light source system, wherein one of the first and second imaging means comprises an electronic camera.

5. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

a flash light source system for providing flash illuminations for photographing adapted to perform two successive emissions of light, a quantity of flash light emitted during one of the two successive emissions corresponding to the sensitivity of the first imaging means and the quantity of flash light emitted during the other of the two successive emissions corresponding to the sensitivity of the second imaging means; and control means for performing successive alternate photographing operations with first and second imaging means corresponding to the two successive emissions in response to only one manual input operation, wherein one of the first and second imaging means comprises an electronic camera.

6. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

a flash light source system for providing flash illuminations for photographing adapted to perform two successive emissions of flash light, a quantity of flash light emitted during one of the two successive emissions corresponding to the sensitivity of the first imaging means and the quantity of flash light emitted during the other of the two successive emissions corresponding to the sensitivity of the second imaging means; and control means for performing successive alternate photographing operations with first and second imaging means corresponding to the two successive emissions in response to only one manual input operation, wherein one of the first and second imaging means comprises means for immediately displaying the image of the eye.

7. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

a flash light source system for providing flash illuminations for photographing adapted to emit a quantity of flash light corresponding to the sensitivity of the first imaging means, and a quantity of flash light corresponding to the sensitivity of the second imaging means; and select means for selecting one of a plurality of photographing modes, said photographing modes at least comprising a mode for alternately performing photographing operations by using the first and second imaging means in response to only common manual input operations, wherein each photographic operation is performed with the quantity of flash light of illumination corresponding to the sensitivity of the imaging means used by said flash light source system, wherein one of the first and second imaging means comprises an electronic camera.

8. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

a flash light source system for providing flash illuminations for photographing adapted to perform alternate emissions of flash light, a quantity of flash light emitted during one of the alternate emissions corresponding to the sensitivity of the first imaging means and the quantity of flash light emitted during the other of the alternate emissions corresponding to the sensitivity of the second imaging means; and control means for performing alternate photographing operations with first and second imaging means corresponding to the alternate emissions in response to common manual input operations, wherein one of the first and second imaging means comprises means for immediately displaying the image of the eye.

9. An ophthalmic apparatus, comprising:

a first photographing system for photographing an image of an eye to be inspected with first imaging means for receiving the image of the eye to be inspected;

a second photographing system for photographing the image of the eye to be inspected with second imaging means for receiving the image of the eye to be inspected having a sensitivity different from the sensitivity of the first imaging means;

a flash light source system for providing flash illuminations for photographing adapted to perform two successive emissions of flash light, a quantity of flash light emitted during one of the two successive emissions corresponding to the sensitivity of the first imaging means and a quantity of flash light emitted during the other of the two successive emissions corresponding to the sensitivity of the second imaging means; and control means for performing successive alternate photographing operations with the first and second imaging means corresponding to the two successive emissions in response to only one manual input operation.

10. An apparatus according to claim 9, wherein said first photographing system photographs the image of the eye with a television camera as the first imaging means, and said second photographing system photographs the image of the eye with a film as the second imaging means.

11. An ophthalmic apparatus, comprising:

a first photographing optical system for guiding an image of an eye to be inspected to first imaging means;

a second photographing optical system for guiding the image of the eye to be inspected to second imaging means having a sensitivity different from the sensitivity of the first imaging means;

control means for performing successive alternate photographing operations with the first and second imaging means in response to only one manual input operation; and a flash light source system for providing two successive flash illuminations corresponding to the two successive alternate photographing operations to emit a quantity of flash light corresponding to the sensitivity of the first imaging means during the photographing operation with the first imaging means, and a quantity of flash light corresponding to the sensitivity of the second imaging means during the photographing operation with the second imaging means.

* * * * *

UNITED STATES PATENT AND TRADEMARK OFFICE
CERTIFICATE OF CORRECTION

PATENT NO. : 5,557,321  
DATED : September 17, 1996  
INVENTOR(S) : Yoshimi KOHAYAKAWA, ET AL.

It is certified that error appears in the above-indentified patent and that said Letters Patent is hereby corrected as shown below:

ON THE COVER PAGE item [54]   Title:

"OPTHALMIC" should read --OPHTHALMIC--.

[56]   References Cited - U.S. PATENT DOCUMENTS:

"4,690,525 9/1987 Kabayashi et al." should read --4,690,525 9/1987 Kobayashi et al.--.

COLUMN 1:

Line 1, "OPTHALMIC" should read --OPHTHALMIC--.
Line 49, "peform" should read --perform-- and.
Line 62, "sescond" should read --second--.

COLUMN 3:

Line 29, "FIG. 5 a" should read --FIG. 5 is a--.
Line 32, "operationsal" should read --operational--.
Line 35, "operationsal" should read --operational-- .
Line 40, "FIG. 8 a" should read --FIG. 8 is a--.

UNITED STATES PATENT AND TRADEMARK OFFICE
CERTIFICATE OF CORRECTION

PATENT NO. : 5,557,321           Page 2 of 2
DATED : September 17, 1996
INVENTOR(S) : Yoshimi KOHAYAKAWA, ET AL.

It is certified that error appears in the above-indentified patent and that said Letters Patent is hereby corrected as shown below:

COLUMN 4:

Line 47, "projeced" should read --projected--.

COLUMN 6:

Line 17, "performated" should read --perforated--.

COLUMN 7:

Line 19, "optical." should read --optical--.

COLUMN 9:

Line 57, "camera." should read --camera--.

Signed and Sealed this

Eleventh Day of March, 1997

Attest:

BRUCE LEHMAN

Attesting Officer        Commissioner of Patents and Trademarks